United States Patent [19]

Elliott et al.

[11] Patent Number: 4,599,454

[45] Date of Patent: Jul. 8, 1986

[54] SYNTHESIS OF KETONES FROM ALCOHOLS

[75] Inventors: David J. Elliott; Filippo Pennella, both of Bartlesville, Okla.

[73] Assignee: Phillips Petroleum Company, Bartlesville, Okla.

[21] Appl. No.: 725,844

[22] Filed: Apr. 22, 1985

[51] Int. Cl.$^4$ .............................................. C07C 45/49
[52] U.S. Cl. .................................... 568/387; 560/232; 568/487; 568/485; 568/840
[58] Field of Search ............... 568/403, 387, 388, 361; 423/656

[56] References Cited

U.S. PATENT DOCUMENTS

| | | | |
|---|---|---|---|
| 2,046,145 | 6/1936 | Arnold | 568/403 |
| 2,419,142 | 4/1946 | Ipatieff et al. | 568/388 |
| 2,526,742 | 10/1950 | Gresham et al. | 568/387 |
| 2,670,378 | 2/1954 | Frye | 568/387 |
| 3,153,068 | 10/1964 | Porter et al. | 568/403 |
| 3,326,956 | 6/1967 | Davies et al. | 260/449.5 |
| 3,361,828 | 1/1968 | Robbins et al. | 568/403 |
| 3,615,217 | 10/1971 | O'Brian et al. | 423/656 |
| 3,790,505 | 2/1974 | Casey et al. | 252/463 |
| 4,052,467 | 10/1977 | Mills et al. | 260/638 B |
| 4,126,581 | 11/1978 | Sugier et al. | 423/656 |
| 4,289,911 | 9/1981 | Isogai et al. | 568/387 |
| 4,380,673 | 4/1983 | Bournonville et al. | 568/361 |
| 4,440,668 | 4/1984 | Chang et al. | 582/331 |
| 4,453,015 | 6/1984 | Slaugh et al. | 568/406 |

*Primary Examiner*—James H. Reamer
*Attorney, Agent, or Firm*—French and Doescher

[57] ABSTRACT

Higher ketones are prepared by contacting, under suitable reaction conditions, a feed stream comprising (a) a primary alcohol of 2-6 carbon atoms per molecule (preferably ethanol, 1-propanol or 1-butanol) and (b) carbon monoxide with a catalyst composition containing copper oxide, zinc oxide and, optionally, alumina.

23 Claims, No Drawings

SYNTHESIS OF KETONES FROM ALCOHOLS

BACKGROUND OF THE INVENTION

This invention relates to a catalytic process for producing ketones. In another aspect, this invention relates to the conversion of primary alcohols to higher ketones.

Processes for converting secondary alcohols to ketons are well known. However, there are no practical processes for directly converting primary alcohols to higher ketones at acceptable yields.

SUMMARY OF THE INVENTION

It is an object of this invention to catalytically convert lower primary aliphatic alcohols, preferably normal alcohols (straight chain alcohols), to ketones containing at least one carbon atom per molecule more than said alcohols. It is another object of this invention to at least partially convert ethanol to at least one higher ketone containing three or more carbon atoms per molecule. It is a further object of this invention to at least partially convert 1-propanol to at least one ketone having four or more carbon atoms per molecule. It is still another object to convert 1-butanol to higher ketones. Other objects and advantages of the invention will be apparent from the detailed description and the appended claims.

In accordance with this invention, a mixture comprising (a) at least one primary alcohol having from 2 to 6 carbon atoms per molecule and (b) carbon monoxide is contacted with a catalyst composition comprising copper(II) oxide and zinc oxide, under such conditions as to at least partially convert said primary alcohol to at least one ketone having at least 1 carbon atom per molecule more than the primary alcohol. Preferably, the primary alcohol is a normal (straight chain) primary alcohol. In one embodiment, the catalyst composition employed in the process of this invention comprises copper oxide, zinc oxide and an inorganic refractory oxide support material (e.g., alumina). In one preferred embodiment, the catalyst composition comprising CuO and ZnO is pretreated by heating with a reducing gas, preferably a free hydrogen containing gas, under such conditions as to partially reduce CuO to $Cu_2O$ and/or Cu metal, before the catalyst composition is used in the process of this invention.

In a further embodiment, a gaseous mixture comprising ethanol and carbon monoxide is passed over a $CuO$—$ZnO$—$Al_2O_3$ containing catalyst composition (preferably having been pretreated by heating with a free hydrogen containing gas), under reaction conditions as to form at least one ketone containing at least 3 carbon atoms per molecule. In still another embodiment, a mixture comprising 1-propanol and carbon monoxide is passed over a $CuO$—$ZnO$—$Al_2O$ containing catalyst composition (preferably having been pretreated by heating with a free hydrogen containing gas), under such reaction conditions as to form at least one ketone containing at least 4 carbon atoms per molecule. In a still further embodiment, a mixture comprising 1-butanol and carbon monoxide is passed over a $CuO$—$ZnO$—$Al_2O_3$ containing catalyst composition (preferably having been pretreated by heating with a free hydrogen containing gas), under suitable reaction conditions as to form at least one ketone containing at least 5 carbon atoms per molecule.

DETAILED DESCRIPTION OF THE INVENTION

The catalyst composition employed in the process of this invention comprises an oxide of copper and an oxide of zinc. Preferably the mixed oxide is prepared by coprecipitation of either the hydroxides of copper and zinc and/or the carbonates of copper and zinc, e.g. by addition of a base such as NaOH, and optionally a soluble carbonate such as $Na_2CO_3$, to an aqueous solution of copper(II) and zinc salts, such as nitrates, sulfates or halides of copper and zinc, and subsequent calcination (e.g., heating in a non-reducing atmosphere, e.g., air) under such conditions as to form the oxides of copper and zinc. In one embodiment, an inert support material such as alumina is also present in said catalyst composition, preferably prepared by either coprecipitation of hydroxides and/or carbonates of copper, zinc and aluminum and subsequent calcination under such conditions as to form the oxides of copper, zinc and aluminum; or by coprecipitation of hydroxides and/or carbonates of copper and zinc from an aqueous solution containing dispersed alumina, and subsequent calcination; or by the method described in U.S. Pat. No. 3,790,505, herein incorporated by reference. CuO—ZnO containing catalyst compositions are commercially available from United Catalysts, Inc., Louisville, Ky. and from BASF from Wyandotte Corporation, Parsippany, N.J.

In a preferred embodiment, the CuO—ZnO and CuO—ZnO—$Al_2O_3$ catalyst compositions are pretreated by heating with a reducing gas, preferably a free hydrogen containing gas, so as to partially reduce CuO. More preferably, said heating is carried out with a free hydrogen containing gas, most preferably a $H_2N_2$ mixture containing 2–5 volume-% $H_2$, at about 350°–450° C. for about 1–6 hours.

Preferably the weight ratio of CuO to ZnO ranges from about 1:20 to about 20:1, more preferably from about 1:3 to about 3:1. If alumina or another inert refractory material (e.g., silica, an alumino-silicate, titania, magnesia and the like) is also present in said catalyst composition, the weight ratio of said inert material such as alumina to (CuO plus ZnO) can range from about 1:100 to about 10:1, preferably from about 1:10 to 2:1. Generally the surface area (determined by the $BET/N_2$ method, ASTM D3037) of the finished catalyst composition ranges from about 20 $m^2/g$ to about 300 $m^2/g$, preferably from about 50 $m^2/g$ to about 200 $m^2/g$.

The gaseous feed mixture that is contacted with the CuO—ZnO containing catalyst composition which comprises (a) at least one primary alcohol having from 2 to 6 carbon atoms per molecule and (b) carbon monoxide. The volume ratio of the alcohol vapor to carbon monoxide gas generally ranges from about 1:100 to about 20:1, preferably from about 1:20 to about 1:1, measured at about 550° F. and 15 psia. An inert gas such as nitrogen or helium can also be present in said feed stream. Preferred primary alcohols are normal primary alcohols, most preferably ethanol, 1-propanol, and 1-butanol.

The alcohol and CO containing mixture can be contacted with the CuO—ZnO containing catalyst composition in any suitable manner. An at least partially vaporized alcohol containing stream and a carbon monoxide containing stream can be passed separately into a suitable reaction vessel and can then be contacted in at least partially mixed form with the catalyst composition under suitable reaction conditions. The alcohol containing stream can be fed as a substantially liquid stream, which will then vaporize in the reactor, or as a substantially vaporized stream. Or the two streams can be premixed and then be contacted with the catalyst composition under suitable reaction conditions so as to produce a reaction product comprising at least one ketone. The process of this invention can be carried out as a batch process or as a continuous process. In a batch process, the process ingredients are charged in any order to a vessel equipped with pressuring and heating means, and the ingredients are then kept in contact with the catalyst composition for a certain length of time under suitable reaction conditions so as to produce a product comprising at least one ketone containing at least 1 C atom per molecule more than the primary alcohol. In this type of operation, the catalyst can be dispersed in the gaseous feed stream as a fluidized bed; or the gaseous feed stream can be circulated through a fixed bed containing the catalyst composition. In a continuous process, which is presently preferred, the alcohol and CO containing gaseous feed stream can be passed, at least partially mixed, through a fixed bed containing the solid catalyst composition, under such conditions as will result in a product comprising at least one ketone. Optionally, an inert gas can be present during the batch or continuous process.

Heating of the process ingredients is generally required to accomplish at least partial conversion of the primary alcohol to a ketone. Any suitable temperature that will cause and maintain a controllable reaction can be employed. Any feasible heating means can be utilized. It is within the scope of this invention to preheat one or more of the process ingredients before they are introduced into a reactor, which is heated to maintained a suitable temperature. The reaction temperature generally ranges from about 200° C. to about 400° C., preferably from about 250° C. to about 300° C.

Any suitable reaction pressure can be employed. The reaction pressure generally is above atmospheric pressure. The selection of the reaction pressure will greatly depend on the reaction temperature, the feed rates of the reactants and the specific reactor design. Generally the pressure ranges from about 1 to about 5000 psig, preferably about 200 to about 200 psig.

The reaction time, i.e., the time of intimate, simultaneous contact of all process ingredients, can vary from 0.01 to about 60 minutes, and will preferably be in the range of about 0.1 to about 10 minutes. The actual reaction time will greatly depend on the flow rates of the alcohol and CO containing feed stream, the selection of an effective, yet safe reaction temperature, the extent of mixing and agitation (if any) during the reaction, the amount of the catalyst employed, etc. In a continuous process, the gas hourly space velocity of the feed mixture comprising the primary alcohol and CO ranges generally from about 100 to about 10,000 cc feed mixture/cc catalyst/hour, preferably from about 1,000 to about 5,000 cc/cc/hr, measured at about 550° F. and 15 psia.

The formed reaction product which comprises at least one ketone having at least 1 carbon atom more than the primary alcohol from which it is formed can be separated from the reaction product by any suitable separation means such as condensation, crystallization, absorption, fractional distillation, or extraction with a suitable solvent plus subsequent evaporation of the solvent. Unreacted process ingredients can be at least partially separated in a similar manner and can be recycled to the reaction zone, where the conversion of a primary alcohol to a ketone in accordance with this invention occurs.

If a reaction product containing more than one ketone is formed, said product can be separated into the pure components by any of the above-cited or other known separation means. Compositions of products formed in the reactions of CO with the preferred alcohols (ethanol, 1-propanol, 1-butanol) under specific reaction conditions are presented in the examples. Ketones prepared by the process of this invention can be used as solvents and/or as reactants in various organic synthesis.

The following examples are presented to further illustrate this invention without unduly limiting the scope of the invention.

EXAMPLE I

This example illustrates the conversion of ethanol and carbon monoxide to higher ketones in the presence of a 16/14 mesh $CuO$—$ZnO$—$Al_2O_3$ catalyst prepared substantially in accordance with the procedure of Example I of U.S. Pat. No. 3,790,505. The reactor used was a vertical, tubular, stainless steel reactor having an inner diameter of about one-half inch and a catalyst bed length of about 5-6 inches, and being heated by means of an outside furnace. The reactor was filled as follows: top layer of 5 cc of 16 mesh Alundum (having a surface area of less than 1 $m^2/g$; marketed by Norton Chemical Process Products, Akron, Ohio); middle layer of 2.5 cc (3.0 g) of the $CuO$—$ZnO$—$Al_2O_3$ plus 7.5 cc 16 mesh Alundum; bottom layer of 5 cc 16 mesh Alundum. A thermocouple was axially inserted into the catalyst bed.

First the catalyst bed in the reactor was pretreated with a $H_2/N_2$ (3/97) gas mixture at about 390°–400° F., for a time period of about 4 hours. Then the reactor was purged with nitrogen, the reactor temperature was raised to about 540°–550° F., and two feed streams were charged to the reactor: liquid ethanol at a rate of 2.13 cc/hour and carbon monoxide (99.5%) at a rate of 140 cc/minute, so as to provide a combined gas stream containing about 90 volume-% CO. The product stream was cooled by a cold trap having a temperature of about 40° F., so as to condense the less volatile components.

The off-gas product stream was analyzed by means of a modified Applied Automation Model 12 gas chromatograph (GC), whereas the liquid product was analyzed by means of a Hewlett-Packard Model 5750 gas chromatograph with columns being packed with Porapak Q material. The various components of the liquid product separated by GC were confirmed by mass spectrometry.

The gaseous product stream (not condensed by the cold trap) comprised 5.8 volume-% of $H_2$, 83.5 volume-% of CO, 7.5 volume-% of $CO_2$ and about 0.4 volume-% of methane and ethane. About 18.4 cc of a condensed (liquid) product was collected during a 16 hour time period. The composition of the liquid product is summarized in Table I.

TABLE I

| Compound | Weight % | Amount Received No. of Milligrams | No. of Millimoles |
|---|---|---|---|
| Water | 0.23 | 9.02 | 0.50 |
| Methanol | 11.47 | 57.62 | 1.80 |
| Acetaldehyde | 0.27 | 10.58 | 0.24 |
| Ethanol | 6.68 | 261.86 | 5.69 |
| Acetone | 0.22 | 8.62 | 0.20 |
| Methyl Acetate | 2.74 | 107.41 | 1.49 |
| 1-Propanol | 1.84 | 72.13 | 1.20 |
| Butanone | 3.63 | 142.30 | 1.98 |
| Methyl Propionate | 3.04 | 119.17 | 1.39 |
| 2-Methyl-1-Propanol | 4.15 | 162.68 | 2.20 |
| 1-Butanol | 2.20 | 86.24 | 1.17 |
| 3-Methyl-2-Butanone | 2.32 | 90.94 | 1.26 |
| Other $C_5$ Ketones | 3.47 | 136.02 | 1.89 |
| Methyl Butyrate | 1.78 | 69.78 | 0.70 |
| Not Identified | 3.41 | 133.67 | 1.52 |
| $C_6$ Alcohols | 4.58 | 179.54 | 2.04 |
| $C_6$ Ketones | 15.48 | 606.82 | 7.05 |
| $C_7$ Ketones | 12.39 | 485.69 | 4.87 |
| $C_8$ Ketones | 18.17 | 717.26 | 6.27 |
| $C_9$ Ketones | 1.93 | 75.66 | 0.59 |
| TOTAL | 100.00 | | 44.05 |

Data in Table I show that the liquid product stream comprised 53.8 weight-% (49.8 mole-%) of ketones having from 5 to 9 C atoms per molecule. Furthermore, only 6.7 weight-% of the liquid product stream was unreacted ethanol indicating an ethanol conversion of about 93%.

EXAMPLE II

This example illustrates the conversion of 1-propanol and carbon monoxide to higher ketone at conditions essentially the same as those described in Example I. The flow rate of the liquid 1-propanol feed stream was 2.13 cc/hour, the CO flow rate was 140 cc/minute. The gaseous product stream comprised 4.0 volume-% of $H_2$, 89 volume-% of CO, 4.4 volume-% of $CO_2$, and about 0.2 volume-% of $C_1$-$C_3$ alkanes. About 24 cc of a condensed (liquid) product was collected during a 16 hour time period. The composition of the liquid product is summarized in Table II.

TABLE II

| Compound | Weight % | Amount Received No. of Milligrams | No. of Millimoles |
|---|---|---|---|
| Water | 0.74 | 36.7 | 2.04 |
| Methanol | 2.37 | 117.6 | 3.68 |
| Propanal | 0.74 | 36.7 | 0.63 |

TABLE II-continued

| Compound | Weight % | Amount Received No. of Milligrams | No. of Millimoles |
|---|---|---|---|
| 1-Propanol | 9.10 | 451.4 | 7.52 |
| Methyl Propanal | 1.02 | 50.6 | 0.70 |
| 2-Methyl-1-Propanol | 11.58 | 574.4 | 7.76 |
| $C_5$ Ketones | 5.84 | 289.7 | 3.37 |
| $C_6$ Alcohols | 7.78 | 385.9 | 3.78 |
| $C_6$ Ethers | 1.18 | 58.5 | 0.57 |
| $C_6$ Ketones[1] | 39.49 | 1958.7 | 19.59 |
| $C_7$ Ketones | 13.78 | 683.5 | 6.00 |
| $C_8$ Ketones | 6.39 | 316.9 | 2.48 |
| $C_9$ Ketones | — | — | — |
| TOTAL | 100.01 | | 58.12 |

[1] Mainly 2-methyl-3-pentanone

Data in Table II show that the liquid product stream comprised 65.5 weight-% (54.1 mole-%) of ketones containing from 5 to 8 C atoms per molecule. Furthermore, the liquid product contained 9.1 weight-% unreacted 1-propanol indicating a propanol conversion of about 91%.

EXAMPLE III

This example illustrates the conversion of 1-butanol and carbon monoxide to higher ketones at conditions essentially the same as those described in Example I. The flow rate of the liquid 1-butanol feed stream was 2.88 cc/hour; the CO flow rate was 140 cc/minute. The gaseous product comprised 4.7 volume-% of $H_2$, 85.5 volume-% of CO, 3.5 volume-% of $CO_2$, and 0.1 volume-% of butene. About 37 cc of liquid product was collected during a 16 hour time period. The composition of the liquid product is summarized in Table III.

TABLE III

| Compound | Weight % | Amount Received No. of Milligrams | No. of Millimoles |
|---|---|---|---|
| Methanol | 3.31 | 261 | 8.16 |
| $C_4$ Hydrocarbons | 0.45 | 35 | 0.63 |
| Butanal | 1.28 | 101 | 1.40 |
| 1-Butanol | 10.55 | 832 | 11.24 |
| Pentanal | 0.37 | 29 | 0.34 |
| $C_5$ Alcohols | 2.82 | 222 | 2.52 |
| Methyl Butyrate | 3.52 | 278 | 2.73 |
| Not Identified[1] | 3.22 | 255 | 2.9 |
| $C_7$ Ketones | 2.80 | 221 | 1.94 |
| Dibutyl Ether | 9.53 | 751 | 5.78 |
| $C_8$ Alcohols | 4.12 | 324 | 2.52 |
| $C_8$ Ketones | 30.66 | 2418 | 18.99 |
| Butyl Butyrate | 16.28 | 1284 | 8.92 |
| $C_9$ Ketones | 4.06 | 320 | 2.21 |
| $C_{10}$ Ketones | 0.77 | 61 | 0.38 |
| Various Alcohols | 1.59 | 125 | 0.79 |
| Various Esters | 3.88 | 306 | 1.85 |
| Not Identified | 0.78 | 62 | 0.39 |
| TOTAL | 99.99 | | 73.59 |

[1] Most likely includes $C_5$-$C_6$ ketones.

Data in Table III show that the liquid stream comprises 38.3 weight-% (31.8 mole-%) of ketones containing from 7 to 10 carbon atoms per molecule and most likely 1-3 weight-% of ketones containing 5-6 carbon atoms per molecule. Furthermore, the liquid product contained 10.6 weight-% -butanol indicating a butanol conversion of about 89%.

Reasonable variations and modifications are possible within the scope of the disclosure and appended claims.

We claim:

1. A process for preparing ketones which comprises the step of contacting a mixture comprising
   (a) at least one alcohol selected from the group consisting of normal primary alcohols having from 2 to 6 carbon atoms per molecule, and
   (b) carbon monoxide with a catalyst composition comprising copper(II) oxide and zinc oxide, under such conditions as to produce a reaction product comprising at least one ketone having at least 1 carbon atoms per molecule more than said at least one alcohol.

2. A process in accordance with claim 1, wherein said catalyst composition also comprises alumina.

3. A process in accordance with claim 1, wherein said at least one alcohol is ethanol.

4. A process in accordance with claim 1, wherein said at least one alcohol is 1-propanol.

5. A process in accordance with claim 1, wherein said at least one alcohol is 1-butanol.

6. A process in accordance with claim 1, wherein the weight ratio of CuO to ZnO in said catalyst composition ranges from about 1:20 to about 20:1, and the surface area of said catalyst composition ranges from about 20 m$^2$/g to about 300 m$^2$/g.

7. A process in accordance with claim 2, wherein the weight ratio of CuO to ZnO in said catalyst composition ranges from about 1:20 to about 20:1, the weight ratio of Al$_2$O$_3$ to (CuO plus ZnO) ranges from about 1:100 to about 10:1, and the surface area of said catalyst composition ranges from about 20 m$^2$/g to about 300 m$^2$/g.

8. A process in accordance with claim 1, wherein the weight ratio of CuO to ZnO in said catalyst composition ranges from about 1:3 to about 3:1, and the surface area of said catalyst composition ranges from about 50 m$^2$/g to about 200 m$^2$/g.

9. A process in accordance with claim 2, wherein the weight ratio of CuO to ZnO in said catalyst composition ranges from about 1:3 to about 3:1, the weight ratio of Al$_2$O$_3$ to (ZnO plus CuO) ranges from about 1:10 to about 2:1, and the surface area of said catalyst composition ranges from about 50 m$^2$/g to about 200 m$^2$/g.

10. A process in accordance with claim 1, wherein said catalyst composition has been pretreated by heating with a reducing gas under such conditions as to partially reduce copper(II) oxide before said contacting.

11. A process in accordance with claim 10, wherein said reducing gas is a free hydrogen containing gas, and said heating conditions comprise a temperature of about 350°–450° F. and a heating time of about 1–6 hours.

12. A process in accordance with claim 1, wherein the volume ratio of said at least one alcohol to carbon monoxide ranges from about 1:100 to about 20:1, measured at about 550° F. and about 15 psia.

13. A process in accordance with claim 6, wherein the volume ratio of said at least one alcohol to carbon monoxide ranges from about 1:20 to about 1:1, measured at about 550° F. and about 15 psia.

14. A process in accordance with claim 2, wherein the volume ratio of said at least one alcohol to carbon monoxide ranges from about 1:100 to about 20:1, measured at about 550° F. and about 15 psia.

15. A process in accordance with claim 7, wherein the volume ratio of said at least one alcohol to carbon monoxide ranges from about 1:20 to about 1:1, measured at about 550° F. and about 15 psia.

16. A process in accordance with claim 12, wherein said conditions comprise a reaction temperature ranging from about 200° to about 400° C., a reaction pressure ranging from about 1 to 5,000 psig, and a contact time of about 0.01 to about 60 minutes.

17. A process in accordance with claim 14, wherein said conditions comprise a reaction temperature ranging from about 200° to about 400° C., a reaction pressure ranging from about 1 to 5,000 psig, and a contact time of about 0.01 to about 60 minutes.

18. A process in accordance with claim 17, wherein said conditions further comprise a combined gas hourly space velocity of said mixture comprising said at least one alcohol and CO ranges from about 100 to about 10,000 cc mixture/cc catalyst/hour, measured at about 550° F. and 15 psia.

19. A process in accordance with claim 12 wherein said at least one alcohol is ethanol.

20. A process in accordance with claim 12, wherein said at least one alcohol is 1-propanol.

21. A process in accordance with claim 12, wherein said at least one alcohol is 1-butanol.

22. A process in accordance with claim 1 comprising the additional step of separating at least a portion of said ketone from said reaction product.

23. A process in accordance with claim 22 comprising the additional step of recycling at least a portion of said reaction product, from which at least a portion of said ketone has been separated, to the reaction zone where the process in accordance with claim 1 occurs.

* * * * *